US012308094B2

(12) United States Patent
Dimon et al.

(10) Patent No.: US 12,308,094 B2
(45) Date of Patent: *May 20, 2025

(54) NEURAL NETWORK FOR PROCESSING APTAMER DATA

(71) Applicant: Google LLC, Mountain View, CA (US)

(72) Inventors: Michelle Therese Hoerner Dimon, Redwood City, CA (US); Marc Berndl, Mountain View, CA (US); Marc Adlai Coram, Stanford, CA (US); Brian Trippe, New York, NY (US); Patrick F. Riley, Los Altos, CA (US); Philip Charles Nelson, San Jose, CA (US)

(73) Assignee: Google LLC, Mountain View, CA (US)

( * ) Notice: Subject to any disclaimer, the term of this patent is extended or adjusted under 35 U.S.C. 154(b) by 105 days.

This patent is subject to a terminal disclaimer.

(21) Appl. No.: 18/307,748

(22) Filed: Apr. 26, 2023

(65) Prior Publication Data
US 2024/0006027 A1   Jan. 4, 2024

Related U.S. Application Data

(63) Continuation of application No. 16/752,513, filed on Jan. 24, 2020, now Pat. No. 11,670,400, which is a (Continued)

(51) Int. Cl.
*G06N 3/08* (2023.01)
*G16B 40/00* (2019.01)
(Continued)

(52) U.S. Cl.
CPC ............ *G16B 40/20* (2019.02); *G06N 3/08* (2013.01); *G16B 40/00* (2019.02); *G16C 20/30* (2019.02); *G06N 3/045* (2023.01)

(58) Field of Classification Search
CPC ........ G06F 19/24; G06N 3/08; G06N 3/0454; G06N 3/02; G06N 3/045; G06N 3/09;
(Continued)

(56) References Cited

U.S. PATENT DOCUMENTS

| 2010/0304991 A1* | 12/2010 | Brown | ............... | C12N 15/1048 |
| | | | | 506/9 |
| 2011/0263459 A1* | 10/2011 | Borer | ................. | C12N 15/1048 |
| | | | | 506/16 |

(Continued)

FOREIGN PATENT DOCUMENTS

| CN | 101434988 | 5/2009 |
| CN | 101896605 | 11/2010 |
| WO | WO 2014144744 | 9/2014 |

OTHER PUBLICATIONS

Alipanahi B et al., "Predicting the sequence specificities of DNA- and RNA-binding proteins by deep learning", nature biotechnology vol. 33, No. 8, Aug. 2015. (Previously supplied). (Year: 2015).*
(Continued)

*Primary Examiner* — Dave Misir
(74) *Attorney, Agent, or Firm* — Fish & Richardson P.C.

(57) ABSTRACT

Methods, systems, and apparatus, including computer programs encoded on computer storage media, for obtaining data defining a sequence for an aptamer, the aptamer comprising a string of nucleobases; encoding the data defining the sequence for the aptamer as a neural network input; and processing the neural network input using a neural network to generate an output that characterizes how strongly the aptamer binds to a particular target molecule, wherein the neural network has been configured through training to receive the data defining the sequence and to process the data to generate predicted outputs that characterize how strongly the aptamer binds to the particular target molecule.

31 Claims, 4 Drawing Sheets

Related U.S. Application Data continuation of application No. 14/921,973, filed on Oct. 23, 2015, now Pat. No. 10,546,650.

(51) Int. Cl.
  *G16B 40/20* (2019.01)
  *G16C 20/30* (2019.01)
  *G06N 3/045* (2023.01)

(58) Field of Classification Search
  CPC .... C12N 15/1048; G16B 40/00; G16B 40/20; G16C 20/30
  USPC .......................................................... 706/16
  See application file for complete search history.

(56) References Cited

U.S. PATENT DOCUMENTS

| | | | |
|---|---|---|---|
| 2012/0101002 A1 | 4/2012 | Riel-Mehan et al. | |
| 2013/0274113 A1* | 10/2013 | Kim | C12N 15/111 506/1 |
| 2015/0119254 A1* | 4/2015 | Hirao | A61K 48/00 506/1 |
| 2015/0291952 A1* | 10/2015 | Craighead | C12N 15/1048 506/1 |
| 2015/0360195 A1* | 12/2015 | Craighead | G01N 33/54386 506/9 |
| 2016/0076021 A1* | 3/2016 | Stojanovic | C12N 15/115 506/9 |
| 2016/0364522 A1* | 12/2016 | Frey | G16B 20/20 |

OTHER PUBLICATIONS

Zhou J. et al., "Predicting effects of noncoding variants with deep learning-based sequence model", nature methods, published online Aug. 24, 2015. (Previously supplied). (Year: 2015).*

Alipanahi et al., "Predicting the sequence specificities of DNA- and RNA-binding proteins by deep learning" nature biotechnology vol. 33, No. 8, Aug. 2015, 87 pages.

Alipanahi et al., "Supplementary Information for Predicting the sequence specificities of DNA- and RNA-binding proteins by deep learning" Nature Biotechnology, vol. 33, No. 8, Jul. 2015, 28 pages.

Chushak et al., "In silico selection of RNA aptamers," Nucleic Acids Res. Jul. 2009, 37(12):e87, 9 pages.

Darmostuk et al., "Current approaches in SELEX: An update to aptamer selection technology," Biotechnology Advances, Nov. 2015, 33(6):1141-1161.

Hoinka et al., "Large scale analysis of the mutational landscape in HT-SELEX improves aptamer discovery," Nucl. Acids Res, Apr. 2015, 9 pages.

Knight et al., "Array-based evolution of DNA aptamers allows modelling of an explicit sequence-fitness landscape," Nucleic Acids Res. Jan. 2009;37(1):e6, 10 pages.

Office Action in Chinese Application No. 201610926056.9, mailed on Sep. 27, 2019, 23 pages (with English translation).

Office Action in Chinese Appln. No. 201610926056.9, mailed on Feb. 26, 2020, 7 pages (with English translation).

Office Action in European Appln. 16194683.5, mailed on May 13, 2019, 8 pages.

Office Action in Indian Application No. 201644035860, mailed on May 11, 2020, 6 pages (with English translation).

Ozer et al., "New Technologies Provide Quantum Changes in the Scale, Speed, and Success of SELEX Methods and Aptamer Characterization," Molecular Therapy—Nucleic Acids (2014) 3, e183, Aug. 2014, 18 pages.

Riley et al., "Large-Scale Machine Learning for Drug Discovery," Google Research Blogspot, Mar. 2, 2015, retrieved on Oct. 23, 2015, retrieved from URL<http://googleresearch.blogspot.com/2015/03/large-scale-machine-learning-for-drug.html>, 8 pages.

Zhou et al., "Predicting effects of noncoding variants with deep learning—based sequence model", nature methods, vol. 12, No. 10, Aug. 2015, 931-934.

* cited by examiner

NEURAL NETWORK FOR PROCESSING APTAMER DATA

CROSS-REFERENCE TO RELATED APPLICATIONS

This is a continuation of U.S. application Ser. No. 16/752,513, filed on Jan. 24, 2020, which is a continuation of U.S. application Ser. No. 14/921,973, filed on Oct. 23, 2015 (now U.S. Pat. No. 10,546,650). The disclosures of the prior applications are considered part of and are incorporated by reference in the disclosure of this application.

BACKGROUND

This specification relates to a neural network for processing aptamer data.

Neural networks are machine learning models that employ one or more layers of models to generate an output, e.g., one or more classifications, for a received input. Some neural networks include one or more hidden layers in addition to an output layer. The output of each hidden layer is used as input to the next layer in the network, i.e., the next hidden layer or the output layer of the network. Each layer of the network generates an output from a received input in accordance with current values of a respective set of parameters.

SUMMARY

In general, this specification describes a neural network for processing aptamer data.

In general, one innovative aspect of the subject matter described in this specification can be embodied in methods that include the actions of obtaining data defining a sequence for an aptamer, the aptamer comprising a string of nucleobases; encoding the data defining the sequence for the aptamer as a neural network input; and processing the neural network input using a neural network to generate an output that characterizes how strongly the aptamer binds to a particular target molecule, wherein the neural network has been configured through training to receive the data defining the sequence and to process the data to generate predicted outputs that characterize how strongly the aptamer binds to the particular target molecule.

Implementations can include one or more of the following features. The output that characterizes how strongly the aptamer binds comprises a plurality of SELEX round outputs, each SELEX round output corresponding to a respective round in an iterative SELEX process, wherein each SELEX round output characterizes how strongly the aptamer binds to the particular target molecule for the corresponding SELEX round. The SELEX round output corresponding to an earlier SELEX round in the iterative SELEX process is a binary value indicating whether the aptamer exists in a pool for use in a subsequent SELEX round. A SELEX round output for a later SELEX round in the SELEX process comprises a high throughput sequencing count of the aptamer, the high throughput sequencing count indicating how strongly the aptamer binds to the particular target molecule. The output that characterizes how strongly the aptamer binds comprises a vector of fluorescence levels, where a brightness of each fluorescence level indicates how strongly the aptamer binds to the particular target molecule. The neural network is a convolutional neural network. The data defining the sequence comprises data specifying secondary structure of the aptamer. The data specifying the secondary structure comprises data specifying a pattern of hydrogen bonds in the aptamer or an energy dot plot matrix of the aptamer. Encoding the data defining the sequence comprises converting the data defining the sequence to a plurality of one-hot vectors, each one-hot vector corresponding to a respective nucleobase in the aptamer. Iteratively applying mutations to the sequence to generate a mutated sequence that has a maximum strength of binding to the particular target molecule, comprising for each of a plurality of iterations: applying a mutation to a current mutated sequence to generate a new mutated sequence; processing the new mutated sequence using the neural network to generate an output that characterizes how strongly the new mutated sequence binds to a particular target molecule; using the neural network to determine whether the output indicates that the new mutated sequence binds stronger than the current mutated sequence; and selecting another mutation to be applied in a next iteration based on whether the output indicates that the new mutated sequence binds stronger than the current mutated sequence.

Another innovative aspect includes obtaining data defining a plurality of sequences for aptamers, each aptamer comprising a string of nucleobases, each sequence having a respective label comprising characteristics of how strongly the respective aptamer binds to a particular target molecule; encoding the data to generate training data for a neural network; and training the neural network on the training data, the neural network configured to output characteristics of how strongly a particular input sequence binds to the particular target molecule.

Implementations can include one or more of the following features. The neural network is configured to output a plurality of SELEX round outputs, each SELEX round output corresponding to a respective round in an iterative SELEX process, wherein each SELEX round output characterizes how strongly an input aptamer binds to the particular target molecule for the corresponding SELEX round. Each label for a respective aptamer in the training data further comprises, a plurality of binary values for the respective aptamer for a respective plurality of SELEX rounds, each binary value for the respective SELEX round indicating whether the aptamer exists in a pool for use in a subsequent SELEX round, and wherein the neural network output further comprises a plurality of binary values for a respective plurality of SELEX rounds, each binary value for the respective SELEX round indicating whether the aptamer exists in a pool for use in a subsequent SELEX round. Each label for a respective aptamer in the training data further comprises, a plurality of high throughput sequencing counts of the respective aptamer for a respective plurality of SELEX rounds, and wherein the neural network output further comprises a plurality of high throughput sequencing counts of the aptamer, each high throughput sequencing count indicating how strongly the aptamer binds to the particular target molecule. One or more labels for a respective aptamer in the training data further comprises, a vector of fluorescence levels for the respective aptamer, and wherein the neural network output further comprises a vector of fluorescence levels, where a brightness of each fluorescence level indicates how strongly the aptamer binds to the particular target molecule. The data defining the plurality of sequences for aptamers comprises, for each aptamer, data specifying secondary structure of the aptamer. The data specifying the secondary structure comprises data specifying a pattern of hydrogen bonds in the aptamer or an energy dot plot matrix of the aptamer.

Particular embodiments of the subject matter described in this specification can be implemented so as to realize one or more of the following advantages. Conventional methods of identifying binding strength between aptamers and a particular target molecule include applying a SELEX process to randomly selected aptamers, which can be labor-intensive and frequently fails to yield an aptamer with strong specific binding. Advantageously, a neural network can predict a binding strength for an input aptamer to a particular target molecule. In particular, the neural network can predict the SELEX round outputs for novel sequences not found in the original random pool. Therefore, instead of requiring the best aptamer to be present in the initial, relatively small, random pool, scientists can predict the aptamer having the strongest specific binding in the set of all possible sequences. Thus, rather than performing multiple SELEX rounds that may or may not yield an aptamer with strong specific binding, the neural network predicts aptamers with strong specific bindings, which reduces cost and testing time. The neural network can also model binding to multiple targets at once, and therefore identify an aptamer that likely binds to the target molecule and not bind to known background molecules. The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
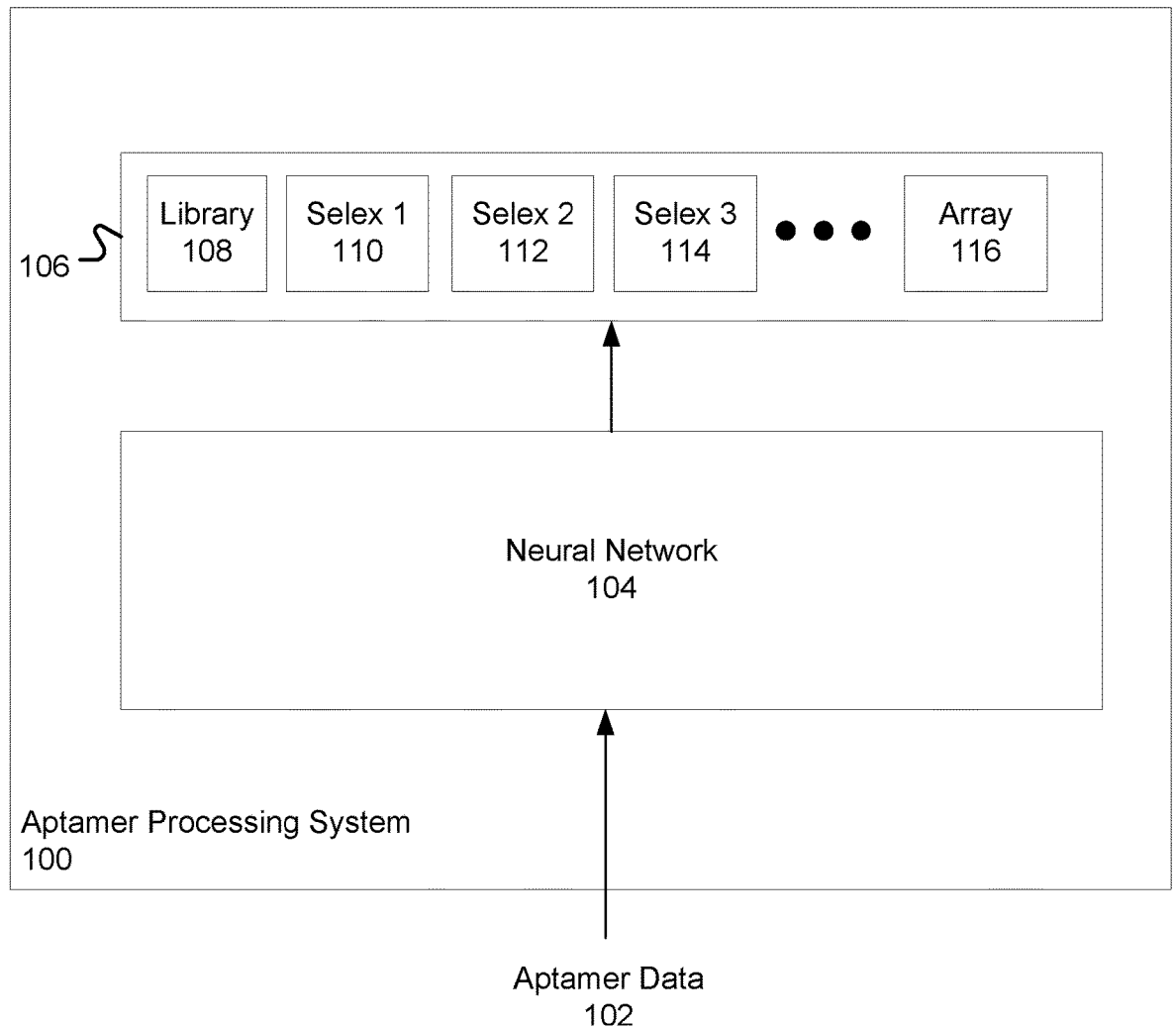
FIG. 1 illustrates an example system for processing aptamer data.

FIG. 1 illustrates an example aptamer processing system 100. The system 100 is an example of a system implemented as computer programs on one or more computers in one or more locations, in which the systems, components, and techniques described below can be implemented.

The system 100 includes a neural network 104. In some implementations, the neural network 104 is a convolutional neural network. The neural network 104 receives aptamer data 102. The aptamer data 102 can be data defining a sequence for an aptamer. An aptamer is a single-stranded molecule that can bind to particular target molecules including proteins and peptides with a degree of affinity, i.e., strength.

The aptamer data can include a sequence of nucleotide bases for an aptamer. In some implementations, the sequence of nucleotide bases is encoded as a sequence of one-hot vectors. For example, a cytosine molecule in the sequence can be represented by a vector [1 0 0 0] while a thymine molecule can be represented by a vector [0 1 0 0].

The vectors can be appended to each other to form a matrix of values, e.g., represented as an image, which can be provided as a tensor input to the neural network 104. For example, if the sequence of nucleotide bases is CTCT, the matrix of values can be the one-hot vectors of the respective nucleotide bases appended together to form the matrix: [1 0 1 0 0 1 0 1 0 0 0 0 0 0 0 0].

By way of illustration, in this example the matrix can be represented as a 4×4 image, where the 1's in the matrix are represented as black pixels and the 0's in the matrix are represented as white pixels. The image representing the matrix can be provided as input to the neural network 104. In some implementations, the neural network 104 performs convolutions on the 4×4 image matrix in a horizontal direction and not a vertical direction. This enables predictions to be based on which nucleotide bases are sequentially adjacent to each other and not based on how one-hot encodings of the nucleotides are implemented. In some other implementations, the matrix is provided as a sequence of bits to the neural network.

The aptamer data can also include data characterizing the secondary structure of the aptamer. For example, the data can specify a pattern of hydrogen bonds in the aptamer or an energy dot plot matrix of the aptamer. Characteristics of the secondary structure can be represented as a byte sequence, e.g., as a one-hot vector or a matrix of values, and provided to the neural network 104. In some implementations, the byte sequence of the secondary structure is appended to the matrix of values formed from the sequence of nucleotide bases to generate the aptamer data that is provided as input to the neural network 104.

The neural network 104 can process the aptamer data 102 to generate an output 106. The output 106 characterizes how strongly the aptamer binds to a particular target molecule. In particular, the output 106 can correspond to outputs generated from a SELEX process for the aptamer data 102.

The SELEX process, i.e., systematic evolution of ligands by exponential enrichment (SELEX), identifies binding strengths to a particular target molecule from a pool of aptamers. In particular, the SELEX process starts with an initial pool of aptamers and processes the pool of aptamers through multiple SELEX rounds. Each SELEX round selects a pool of aptamers that bind the target molecule and discards aptamers that do not bind to the target molecule. After each SELEX round, the resulting pool is amplified using polymerase chain reaction (PCR). During PCR, aptamers with stronger binding strengths tend to be replicated more frequently than aptamers with weaker binding strengths.

After numerous SELEX rounds, a composition of the pool of aptamers indicates a convergence to a small number, e.g., on the order of thousands, of aptamers with high counts, which can potentially indicate a strong binding strength to a target molecule.

By way of illustration, for a SELEX process, the initial pool can have a size on the order of $10^{13}$ aptamers. The initial pool can be referred to as the library of aptamers. The pool can be composed of nearly entirely unique aptamers. After a first SELEX round, i.e., after discarding aptamers that do not bind to a target molecule and enriching aptamers that do bind, the pool can be 99.3% unique. After a second SELEX round, the pool can be 90% unique and have a size on the order of $10^8$ aptamers. After another SELEX round, the pool can be less than 10% unique and have a size on the order of $10^6$ aptamers. After yet another SELEX round, the pool can be less than 5% unique and have a size on the order of $10^5$ aptamers. After each SELEX round, the pool can undergo high throughput sequencing to identify aptamers in the SELEX round having high counts.

As described above, the output 106 corresponds to the outputs from the SELEX process for the aptamer data 102. In other words, the neural network 104 predicts, after each SELEX round, how strongly the input aptamer in the aptamer data 102 binds to the target molecule.

Thus, the output 106 can include a library output 108. In some implementations, the library output 108 is a binary value, e.g., true or false, of whether the input aptamer exists in the initial pool of aptamers. In some other implementations, the library output 108 is a confidence value between 0 and 1 that represents a likelihood that the input aptamer exists in the initial pool of aptamers.

The output 106 can include SELEX 1 output 110. Selex 1 output 110 is the output after performing a first SELEX round in the SELEX process. Selex 1 output 110 can also be a confidence value or a binary value of whether the input aptamer exists in the pool of aptamers after the first round. In some implementations, the neural network 104 generates binary or confidence values for SELEX outputs that are in pools with a percentage of unique aptamers over a particular threshold. This is because a pool of aptamers with a high unique aptamer percentage generally does not have high aptamer count for one particular aptamer, and thus does not indicate any particular aptamer with a high binding strength to the target molecule.

The output 106 can include a SELEX 2 output and a SELEX 3 output 112, 114. Selex 2 and 3 output 112, 114 are outputs after performing a second and third SELEX round, respectively. The output for a respective one of these SELEX rounds can be a predicted count of a number of input aptamers in the respective SELEX round.

In some implementations, the neural network 104 generates, in the output 106, an array or vector of fluorescent values 116. The fluorescent values represent a brightness, which indicates how strongly the input aptamer binds to the target molecule as measured in a binding array.

To generate the output 106, the system 100 can train the neural network 101 using conventional neural network training techniques, which will be described further below with reference to FIG. 2.

Figure 2:
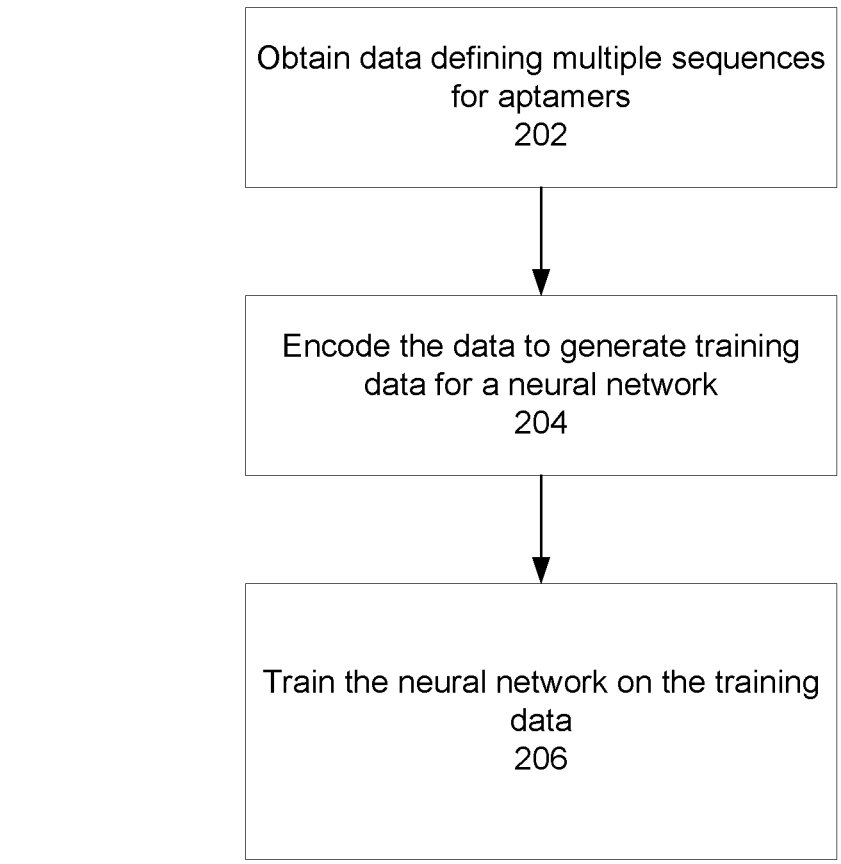
FIG. 2 is a flow diagram of an example method for training a neural network on aptamer data.

FIG. 2 is a flow diagram of an example process 200 for training a neural network on aptamer data. For convenience, the process 200 will be described with respect to a system, e.g., the system 100 of FIG. 1, having one or more computing devices that execute software to implement the process 200.

The system obtains data defining multiple sequences for aptamers (step 202). Each sequence can be represented as multiple one-hot vectors, as described above with reference to FIG. 1.

Each sequence can also have a respective label that includes characteristics of how strongly the respective aptamer binds to a particular target molecule. A label can have the data specified by the output 106 of FIG. 1.

In particular, the label can include binary values for the respective aptamer for earlier SELEX rounds. The binary values can indicate whether the aptamer exists in a pool of aptamers for the round, and thus, whether the aptamer exists in a pool for use in a subsequent SELEX round. The label can also include high throughput sequencing counts of the respective aptamer for later SELEX rounds. In some implementations, the labels also include data of vectors of fluorescence levels for the aptamer. These vectors of fluorescence levels can be obtained through binding array measurements. In some other implementations, the labels include vectors of binding affinity values, where each binding affinity value corresponds to a likelihood of binding to a respective target molecule.

The system encodes the data to generate training data for a neural network (step 204). The system can encode the data defining the sequence by converting the data to multiple one-hot vectors, as described above with reference to FIG. 1.

The system trains the neural network on the training data (step 206). That is, the system processes the training data, e.g., the encoded sequence data, to generate predicted outputs. The system determines an error between each predicted output and a corresponding portion of the label. The system uses the error to update values of the parameters used in each layer of the neural network using conventional neural network training techniques, e.g., stochastic gradient descent with backpropagation. After training, the neural network can generate outputs, e.g., the output 106 of FIG. 1, from input aptamer data.

Figure 3:
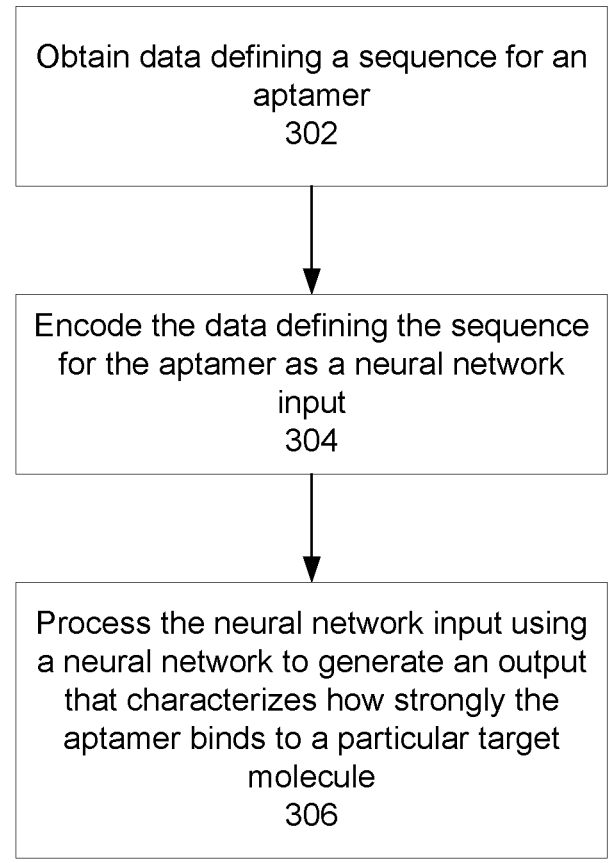
FIG. 3 is a flow diagram of an example method for processing aptamer data using a neural network.

FIG. 3 is a flow diagram of an example process 300 for processing aptamer data using a neural network. For convenience, the process 300 will be described with respect to a system, e.g., the system 100 of FIG. 1, having one or more computing devices that execute software to implement the process 300.

The system obtains data defining a sequence for an aptamer (step 302). Each sequence can be represented as multiple one-hot vectors, as described above with reference to FIG. 1. In some implementations, the data is an image representing the sequence. The image can have black and white pixels as described above with reference to FIG. 1. Additionally, in some implementations, the data also includes data encoding secondary structure of the aptamer.

The system encodes the data defining the sequence as a neural network input (step 304). The system can encode the data defining the sequence by converting the data to multiple one-hot vectors, as described above with reference to FIG. 1.

The system processes the neural network input using a neural network to generate an output that characterizes how strongly the aptamer binds to a particular target molecule (step 306). The neural network can be trained, as described above with reference to FIG. 2. The output that characterizes how strongly the aptamer binds to the particular target molecule can correspond to SELEX round outputs.

Each SELEX round output can correspond to a respective round in an iterative SELEX process, as described above with reference to FIG. 1. That is, the system can generate an output including binary values for a first few SELEX round outputs and numerical values for later SELEX round outputs. The binary values can indicate whether the aptamer exists in a pool for use in subsequent SELEX rounds. The numerical values for the later SELEX round outputs can be predicted counts, e.g., obtained through high throughput sequencing, of the aptamer within a respective pool in the respective SELEX round.

In some implementations, the output also includes an array output of a vector of fluorescent values.

Although the output, e.g., the output 106 of FIG. 1, indicates how strongly an input aptamer binds to a particular target molecule, there may be aptamers similar to the input aptamer that bind more strongly to the particular target molecule. To identify these stronger aptamers, after generating the output, the system can iteratively apply mutations to the sequence of an input aptamer to identify a mutated sequence that has a maximum strength of binding to the particular target molecule. This iterative process can identify aptamers with high binding strength even if the aptamers were not in the initial pool during the SELEX process.

Figure 4:
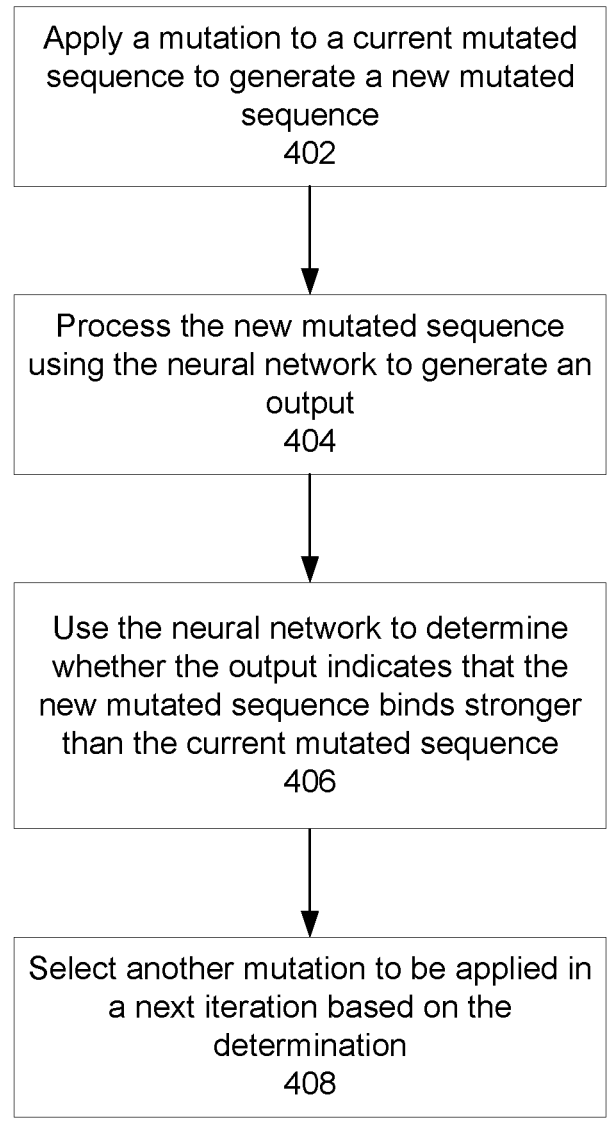
FIG. 4 is a flow diagram of an example process for identifying new mutations to aptamers through an iterative process using a neural network.

FIG. 4 is a flow diagram of an example process 400 for identifying new mutations to aptamers through an iterative process using a neural network. For convenience, the process 400 will be described with respect to a system, e.g., the system 100 of FIG. 1, having one or more computing devices that execute software to implement the process 400.

For each iteration, the system applies a mutation to a current mutated sequence, i.e., the sequence of the input aptamer in the first iteration, to generate a new mutated sequence (step 402). The mutation can randomly change a number of nucleotide bases in the sequence. For example, the mutation can randomly select two nucleotide bases and change them to two other nucleotide bases.

The system can process the new mutated sequence using the neural network to generate another output that characterizes how strongly the new mutated sequence binds to a particular target molecule (step 404), e.g., as described above with reference to FIG. 3.

The system uses the neural network to determine whether the output indicates that the new mutated sequence binds stronger than the current mutated sequence (step 406). That is, the system can compare a high throughput sequencing count for a particular SELEX round of the current mutated sequence with that of the new mutated sequence. If the high throughput sequencing count for the new mutated sequence is higher than that of the current mutated sequence, the system determines the new mutated sequence binds more strongly to the target molecule than the current mutated sequence. Otherwise, the system determines the current mutated sequence binds more strongly to the target molecule than the new mutated sequence. In some implementations, the system factors in high throughput sequencing counts between the current mutated sequence and the new mutated sequence across multiple SELEX rounds. By way of illustration, the system can compute weighted sums of high throughput sequencing counts across multiple SELEX rounds for each sequence to determine which sequence more strongly binds to the target molecule.

The system selects another mutation to be applied in a next iteration based on whether the output indicates that the new mutated sequence binds stronger than the current mutated sequence (step 408). That is, if the new mutated sequence binds more strongly than the current mutated sequence, the system randomly mutates the new mutated sequence and repeats the process described above. Otherwise, the system randomly mutates the current mutated sequence and repeats the process described above. In some implementations, the system mutates the current mutated sequence to a sequence not previously processed. The system can continue mutating sequences until the system generates a threshold number of new mutated sequences or if a higher binding strength is not found for a threshold number of iterations.

The system can repeat the process for a predetermined number of times. Alternatively, the system can repeat the process until the system iterates on the current mutated sequence for a threshold number of times. In other words, the system stops repeating the process when the system is unable to generate, within the threshold number of times, a new mutated sequence that binds more strongly than the current mutated sequence.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) monitor, an LCD (liquid crystal display) monitor, or an OLED display, for displaying information to the user, as well as input devices for providing input to the computer, e.g., a keyboard, a mouse, or a presence sensitive display or other surface. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending resources to and receiving resources from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination.

Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A computer-implemented method for training a neural network to model results of an iterative SELEX process, wherein the iterative SELEX process begins with an initial pool of aptamers and iteratively updates the pool of aptamers at each of a plurality of different rounds, the method comprising:
    obtaining results of the iterative SELEX process applied to the initial pool of aptamers;
    obtaining data defining a plurality of sequences for a plurality of aptamers in the initial pool of aptamers, each aptamer from the plurality of aptamers comprising a string of nucleobases;
    generating, based on the results of the iterative SELEX process, a respective label for each sequence from the plurality of sequences that comprises characteristics of how strongly the respective aptamer binds to at least one target molecule, wherein the respective label for each sequence from the plurality of sequences includes a plurality of sub-labels and each sub-label corresponds to a different round in the iterative SELEX process and characterizes a result of the corresponding round for the respective aptamer;

generating training data for a neural network from the data defining the plurality of sequences and the respective labels for each of the sequences; and training the neural network on the training data, the neural network configured to generate, for a particular aptamer, a model output that comprises a plurality neural network outputs, each neural network output corresponding to a different round in the iterative SELEX process, and, wherein:

each neural network output is a prediction of a result of the corresponding SELEX round, if the particular aptamer were in the initial pool of aptamers as of the beginning of the corresponding SELEX round, and the neural network output corresponding to a first SELEX round in the iterative SELEX process comprises a count, a binary value or a confidence value indicating whether the particular aptamer would exist in the pool of aptamers at completion of the first SELEX round.

2. The method of claim 1, wherein the neural network output corresponding to the first SELEX round in the iterative SELEX process comprises the binary value or the confidence value indicating whether the particular aptamer would exist in the pool of aptamers at completion of the first SELEX round.

3. The method of claim 1, wherein the count is a numerical value that represents a predicted count of the particular aptamer in the pool of aptamers for the first SELEX round.

4. The method of claim 1, wherein the model output comprises a vector of fluorescence levels, where a brightness of each fluorescence level indicates how strongly the particular aptamer binds to the at least one target molecule.

5. The method of claim 1, wherein the neural network is a convolutional neural network.

6. The method of claim 1, wherein the data defining the plurality of sequences comprises, for each aptamer from the plurality of aptamers in the initial pool, data specifying secondary structure of the respective aptamer.

7. The method of claim 6, wherein the data specifying the secondary structure comprises data specifying a pattern of hydrogen bonds in the respective aptamer or an energy dot plot matrix of the respective aptamer.

8. The method of claim 1, wherein the neural network is configured process, for the particular aptamer, an encoding of data defining a sequence for the particular aptamer, the encoding comprising a plurality of one-hot vectors, each one-hot vector corresponding to a respective nucleobase in the particular aptamer.

9. The method of claim 2, wherein the first SELEX round is before a second SELEX round in the iterative SELEX process.

10. A system comprising one or more computers and one or more storage devices storing instructions that when executed by one or more computers cause the one or more computers to perform operations for training a neural network to model results of an iterative SELEX process, wherein the iterative SELEX process begins with an initial pool of aptamers and iteratively updates the pool of aptamers at each of a plurality of different rounds, the operations comprising:

obtaining results of the iterative SELEX process applied to the initial pool of aptamers;

obtaining data defining a plurality of sequences for a plurality of aptamers in the initial pool of aptamers, each aptamer from the plurality of aptamers comprising a string of nucleobases;

generating, based on the results of the iterative SELEX process, a respective label for each sequence from the plurality of sequences that comprises characteristics of how strongly the respective aptamer binds to at least one target molecule, wherein the respective label for each sequence from the plurality of sequences includes a plurality of sub-labels and each sub-label corresponds to a different round in the iterative SELEX process and characterizes a result of the corresponding round for the respective aptamer;

generating training data for a neural network from the data defining the plurality of sequences and the respective labels for each of the sequences; and training the neural network on the training data, the neural network configured to generate, for a particular aptamer, a model output that comprises a plurality neural network outputs, each neural network output corresponding to a different round in the iterative SELEX process, and, wherein:

each neural network output is a prediction of a result of the corresponding SELEX round, if the particular aptamer were in the initial pool of aptamers as of the beginning of the corresponding SELEX round, and the neural network output corresponding to a first SELEX round in the iterative SELEX process comprises a count, a binary value or a confidence value indicating whether the particular aptamer would exist in the pool of aptamers at completion of the first SELEX round.

11. The system of claim 10, wherein the neural network output corresponding to the first SELEX round in the iterative SELEX process comprises the binary value or the confidence value indicating whether the particular aptamer would exist in the pool of aptamers at completion of the first SELEX round.

12. The system of claim 10, wherein the count is a numerical value that represents a predicted count of the particular aptamer in the pool of aptamers for the first SELEX round.

13. The system of claim 10, wherein the model output comprises a vector of fluorescence levels, where a brightness of each fluorescence level indicates how strongly the particular aptamer binds to the at least one target molecule.

14. The system of claim 10, wherein the neural network is a convolutional neural network.

15. The system of claim 10, wherein the data defining the plurality of sequences comprises, for each aptamer from the plurality of aptamers in the initial pool, data specifying secondary structure of the respective aptamer.

16. The system of claim 15, wherein the data specifying the secondary structure comprises data specifying a pattern of hydrogen bonds in the respective aptamer or an energy dot plot matrix of the respective aptamer.

17. The system of claim 10, wherein the neural network is configured process, for the particular aptamer, an encoding of data defining a sequence for the particular aptamer, the encoding comprising a plurality of one-hot vectors, each one-hot vector corresponding to a respective nucleobase in the particular aptamer.

18. The system of claim 10, wherein the first SELEX round is before a second SELEX round in the iterative SELEX process.

19. A system comprising:
one or more computers; and one or more storage devices storing instructions, which, when executed by the one or more computers, cause the one or more computers to perform operations for modeling, for a particular aptamer and at least one target molecule, the results of an iterative SELEX process that begins with an initial pool of aptamers and iteratively updates the initial pool of aptamers at each of a plurality of rounds, the operations comprising:
obtaining data defining a sequence for the particular aptamer, the aptamer comprising a string of nucleobases;
encoding the data defining the sequence for the particular aptamer as a neural network input; and
processing the neural network input using a trained neural network to generate an output that comprises a plurality of neural network outputs, wherein:
each neural network output corresponds to a different one of the plurality of rounds in the iterative SELEX process, and
each neural network output is a prediction of a result of the corresponding SELEX round, if the particular aptamer were in the initial pool of aptamers as of the beginning of the corresponding SELEX round, wherein the neural network output corresponding to a first SELEX round in the iterative SELEX process comprises a characterization of how strongly the particular aptamer would bind to a particular target molecule in the first SELEX round if the particular aptamer were in the initial pool of aptamers as of the beginning of the first SELEX round.

20. The system of claim 19, wherein the neural network output corresponding to the first SELEX round in the iterative SELEX process comprises a binary value or a confidence value indicating whether the particular aptamer would exist in the pool of aptamers at completion of the first SELEX round.

21. The system of claim 20, wherein the neural network output corresponding to a second SELEX round in the iterative SELEX process comprises a numerical value that represents predicted count of the particular aptamer in the pool of aptamers for the second SELEX round, and
the second SELEX round is after the first SELEX round in the iterative SELEX process.

22. The system of claim 19, wherein the output comprises a vector of fluorescence levels, where a brightness of each fluorescence level indicates how strongly the particular aptamer binds to the at least one target molecule.

23. The system of claim 19, wherein the neural network is a convolutional neural network.

24. The system of claim 19, wherein the data defining the sequence comprises data specifying secondary structure of the particular aptamer.

25. The system of claim 24, wherein the data specifying the secondary structure comprises data specifying a pattern of hydrogen bonds in the particular aptamer or an energy dot plot matrix of the particular aptamer.

26. The system of claim 19, wherein encoding the data defining the sequence comprises converting the data defining the sequence to a plurality of one-hot vectors, each one-hot vector corresponding to a respective nucleobase in the particular aptamer.

27. One or more non-transitory computer-readable media storing instructions, which, when executed by one or more computers, cause the one or more computers to perform operations for modeling, for a particular aptamer and at least one target molecule, the results of an iterative SELEX process that begins with an initial pool of aptamers and iteratively updates the initial pool of aptamers at each of a plurality of rounds, the operations comprising:
obtaining data defining a sequence for the particular aptamer, the aptamer comprising a string of nucleobases;
encoding the data defining the sequence for the particular aptamer as a neural network input; and
processing the neural network input using a trained neural network to generate an output that comprises a plurality of neural network outputs, wherein:
each neural network output corresponds to a different one of the plurality of rounds in the iterative SELEX process, and
each neural network output is a prediction of a result of the corresponding SELEX round, if the particular aptamer were in the initial pool of aptamers as of the beginning of the corresponding SELEX round, wherein the neural network output corresponding to a first SELEX round in the iterative SELEX process comprises a characterization of how strongly the particular aptamer would bind to a particular target molecule in the first SELEX round if the particular aptamer were in the initial pool of aptamers as of the beginning of the first SELEX round.

28. The non-transitory computer-readable media of claim 27, wherein the neural network output corresponding to the first SELEX round in the iterative SELEX process comprises a binary value or a confidence value indicating whether the particular aptamer would exist in the pool of aptamers at completion of the first SELEX round.

29. The non-transitory computer-readable media of claim 28, wherein the neural network output corresponding to a second SELEX round in the iterative SELEX process comprises a numerical value that represents predicted count of the particular aptamer in the pool of aptamers for the second SELEX round, and
the second SELEX round is after the first SELEX round in the iterative SELEX process.

30. One or more non-transitory computer-readable storage media storing instructions that when executed by one or more computers cause the one or more computers to perform operations for training a neural network to model results of an iterative SELEX process, wherein the iterative SELEX process begins with an initial pool of aptamers and iteratively updates the pool of aptamers at each of a plurality of different rounds, the operations comprising:
obtaining results of the iterative SELEX process applied to the initial pool of aptamers;
obtaining data defining a plurality of sequences for a plurality of aptamers in the initial pool of aptamers, each aptamer from the plurality of aptamers comprising a string of nucleobases;
generating, based on the results of the iterative SELEX process, a respective label for each sequence from the plurality of sequences that comprises characteristics of how strongly the respective aptamer binds to at least one target molecule, wherein the respective label for each sequence from the plurality of sequences includes a plurality of sub-labels and each sub-label corresponds to a different round in the iterative SELEX process and characterizes a result of the corresponding round for the respective aptamer;
generating training data for a neural network from the data defining the plurality of sequences and the respective labels for each of the sequences; and
training the neural network on the training data, the neural network configured to generate, for a particular aptamer, a model output that comprises a plurality neural network outputs, each neural network output corresponding to a different round in the iterative SELEX process, and, wherein:

each neural network output is a prediction of a result of the corresponding SELEX round, if the particular aptamer were in the initial pool of aptamers as of the beginning of the corresponding SELEX round, and the neural network output corresponding to a first SELEX round in the iterative SELEX process comprises a count, a binary value or a confidence value indicating whether the particular aptamer would exist in the pool of aptamers at completion of the first SELEX round.

31. The one or more non-transitory computer-readable storage media of claim 30, wherein the neural network output corresponding to the first SELEX round in the iterative SELEX process comprises the binary value or the confidence value indicating whether the particular aptamer would exist in the pool of aptamers at completion of the first SELEX round.

\* \* \* \* \*